ns(12) United States Patent
Grinvald et al.

(10) Patent No.: US 8,521,260 B2
(45) Date of Patent: Aug. 27, 2013

(54) CHARACTERIZATION OF ARTERIOSCLEROSIS BY OPTICAL IMAGING

(75) Inventors: Amiram Grinvald, Rehovot (IL); Darin Arnold Nelson, Rehovot (IL); Ivo Vanzetta, Marseilles (FR)

(73) Assignee: Yeda Research and Development Co. Ltd., Rehovot (IL)

( * ) Notice: Subject to any disclaimer, the term of this patent is extended or adjusted under 35 U.S.C. 154(b) by 1523 days.

(21) Appl. No.: 10/537,116

(22) PCT Filed: Dec. 2, 2003

(86) PCT No.: PCT/IL03/01020
§ 371 (c)(1),
(2), (4) Date: Nov. 16, 2005

(87) PCT Pub. No.: WO2004/049899
PCT Pub. Date: Jun. 17, 2004

(65) Prior Publication Data
US 2006/0147897 A1  Jul. 6, 2006

Related U.S. Application Data

(60) Provisional application No. 60/430,268, filed on Dec. 2, 2002.

(51) Int. Cl.
*A61B 6/00* (2006.01)
*A61B 5/02* (2006.01)
*G06K 9/00* (2006.01)

(52) U.S. Cl.
USPC ........... 600/476; 600/473; 600/479; 600/481; 382/128

(58) Field of Classification Search
USPC .............. 600/465, 473, 481, 476, 479, 425; 382/128
See application file for complete search history.

(56) References Cited

U.S. PATENT DOCUMENTS 4,718,417 A   1/1988 Kittrell et al.
5,240,006 A   8/1993 Fujii et al.
(Continued)

FOREIGN PATENT DOCUMENTS
JP    7-163534    6/1995
JP    2002-517269    6/2002
(Continued)

OTHER PUBLICATIONS

Taylor, Charles A. et al., "Finite Element Modeling of Three-Dimensional Pulsatile Flow in the Abdominal Aorta: Relevance to Atherscterosis", Annals of Biomedical Engineering, vol. 26, pp. 975-987.*

(Continued)

*Primary Examiner* — Long V. Le
*Assistant Examiner* — Katherine Fernandez
(74) *Attorney, Agent, or Firm* — Ladas & Parry LLP

(57) ABSTRACT

A method and system for detecting abnormalities in the properties of the walls of a subject's blood vessels by observing the characteristics of blood flow in vessels which are optically accessible, such as the retinal vasculature. A time sequenced series of images is taken, and the images are processed to eliminate the background and render erythrocyte motion visible. Information about the state of the inner wall of the blood vessel which has been imaged is obtained from the characteristics of this blood flow. This information can be extrapolated to provide information about the state of the blood vessels elsewhere in the subject. In addition, a system and method is described for detecting arteriosclerotic plaque on the walls of blood vessels by labeling the plaque with a molecular label having desired optical or radioactive properties, and directly imaging the plaque either in an optically accessible blood vessel, or by imaging radioactive label in the plaque in a blood vessel anywhere in the body.

29 Claims, 8 Drawing Sheets

(56) References Cited

U.S. PATENT DOCUMENTS

| | | | |
|---|---|---|---|
| 5,279,298 A * | 1/1994 | Flower | 600/321 |
| 5,463,426 A | 10/1995 | Grinvald | |
| 5,477,858 A * | 12/1995 | Norris et al. | 600/441 |
| 5,720,291 A | 2/1998 | Schwartz | |
| 5,727,561 A * | 3/1998 | Owsley | 600/504 |
| 5,784,162 A | 7/1998 | Cabib et al. | |
| 5,811,814 A * | 9/1998 | Leone et al. | 250/368 |
| 5,983,120 A | 11/1999 | Groner et al. | |
| 6,104,939 A | 8/2000 | Groner et al. | |
| 6,351,663 B1 * | 2/2002 | Flower et al. | 600/476 |
| 6,588,901 B1 | 7/2003 | Grinvald et al. | |
| 6,782,289 B1 * | 8/2004 | Strauss | 600/436 |
| 6,902,935 B2 | 6/2005 | Kaufman | |
| 2001/0031920 A1 | 10/2001 | Kaufman et al. | |
| 2002/0016533 A1 | 2/2002 | Marchitto et al. | |
| 2002/0111545 A1 | 8/2002 | Lindberg et al. | |
| 2006/0122524 A1 | 6/2006 | Kawada et al. | |

FOREIGN PATENT DOCUMENTS

| | | |
|---|---|---|
| WO | 99/63882 | 12/1999 |
| WO | WO 99/63882 | 12/1999 |
| WO | WO 00/06015 | 2/2000 |

OTHER PUBLICATIONS

Taylor, Charles A. et al. "In Vivo Quantification of Blood Flow and Wall Shear Stress in the Human Abdominal Aorta During Lower Limb Exercise", Annals of Biomedical Engineering, vol. 30, pp. 402-408.*

Zarins et al., "Carotid bifurcation atherosclerosis. Quantitative Correlation of Plaque Localization with Flow Velocity Profiles and Wall Shear Stress", Circ. Res., 1983; 53; pp. 502-514.*

H.H. Quick, et al., "MR Imaging of the Vessel wall", Published in Eur. Radiol, vol. 12(4), pp. 889-900, Apr. 2002.

Dormandy, et al., "Lower-extremity arteriosclerosis as a reflection of a systemic process: implications for concomitant coronary and carotid disease", Published in Semin. Vase. Surg. pp. 118-122, vol. 12(2), Jun. 1999.

Kutzner, et al., "Fatal lipid embolism following intra-arterial angiography at an early stage of anteriosclerosis", Published in British Journal of Radiology, vol. 73 (874), pp. 1108-1111, Oct. 2000.

Wong T.Y. et al., "Retinal microvascular abnormalities and incident stroke: the atherosclerosis risk in communities study", Lancet, 358 (9288), pp. 1134-1140, 2001.

Wong T.Y. et al., "Retinal arteriolar narrowing and risk coronary heart disease in men and women. The atherosclerosis risk in communities study", JAMA; 287(9), pp. 1153-1159, 2002.

Wong T.Y. et al., "White matter lesions, retinopathy, and incident clinical stroke", JAMA 288(1), pp. 67-74, 2002.

"Finite element modeling of three-dimensional pulsatile flow in the abdominal aorta: Relevance to atherosclerosis," Taylor et al., Annals of Biomedical Engineering, vol. 26, pp. 975-987, 1998.

"In vivo quantification of blood flow and wall shear stress in the human abdominal aorta during lower limb exercise," Taylor et al., Annals of Biomedical Engineering, vol. 30, pp. 402-408, 2002.

"Automatic extraction and measurement of leukocyte motion in microvessel using spatiotemporal image analysis," Sato et al., IEEE Transactions on Biomedical Engineering, IEE Inc New York, US, vol. 44, No. 4, Apr. 1, 1997, pp. 225-236.

U. Seifert, W. Visler, "Retinal Vessel Analyzer (RVA)—Design and Function", Biomed Tech vol. 47, Suppl. 1, 2002.

WO 99/63882 dated Dec. 16, 1999 is the English equivalent of JP 2002-517269.

An Office Action dated Nov. 17, 2009, which issued during the prosecution of Applicant's Japanese Patent Application No. 2004-556741.

A computer translation of JP 07-163534, Jun. 1995.

* cited by examiner

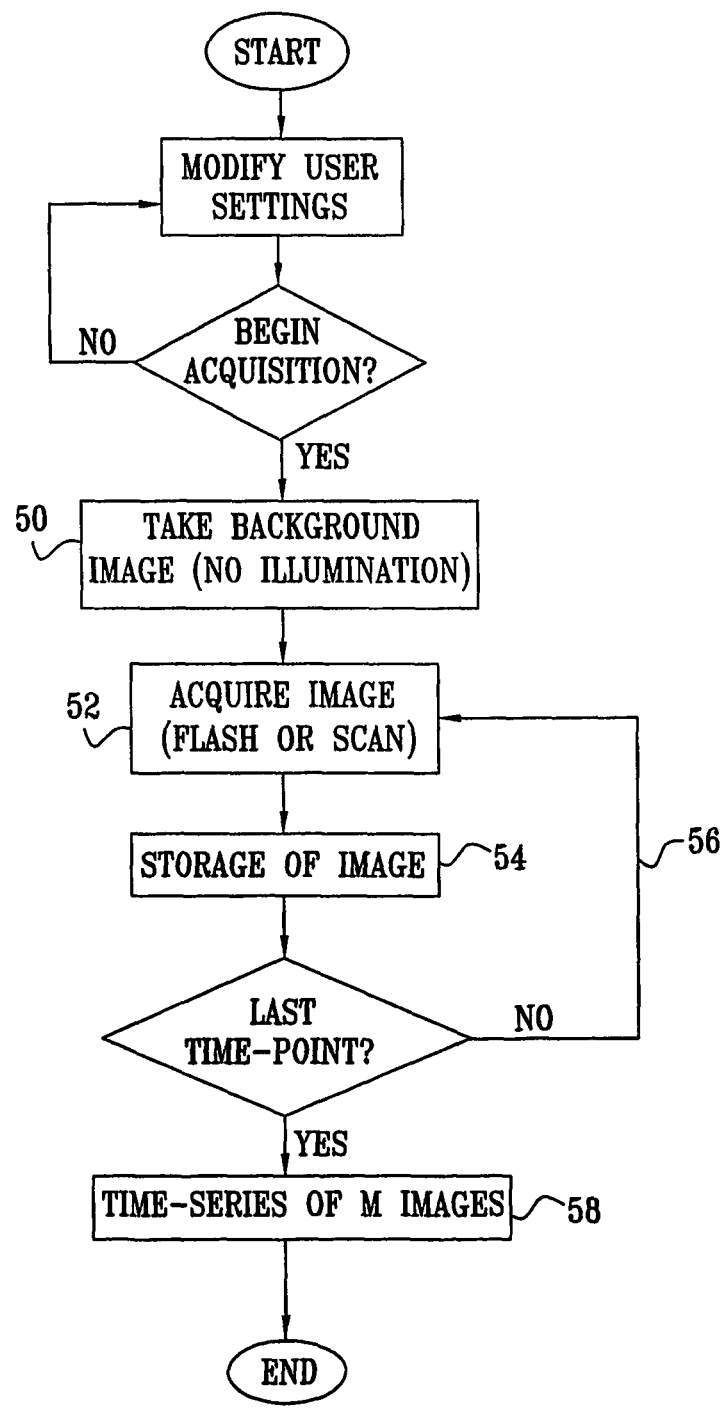

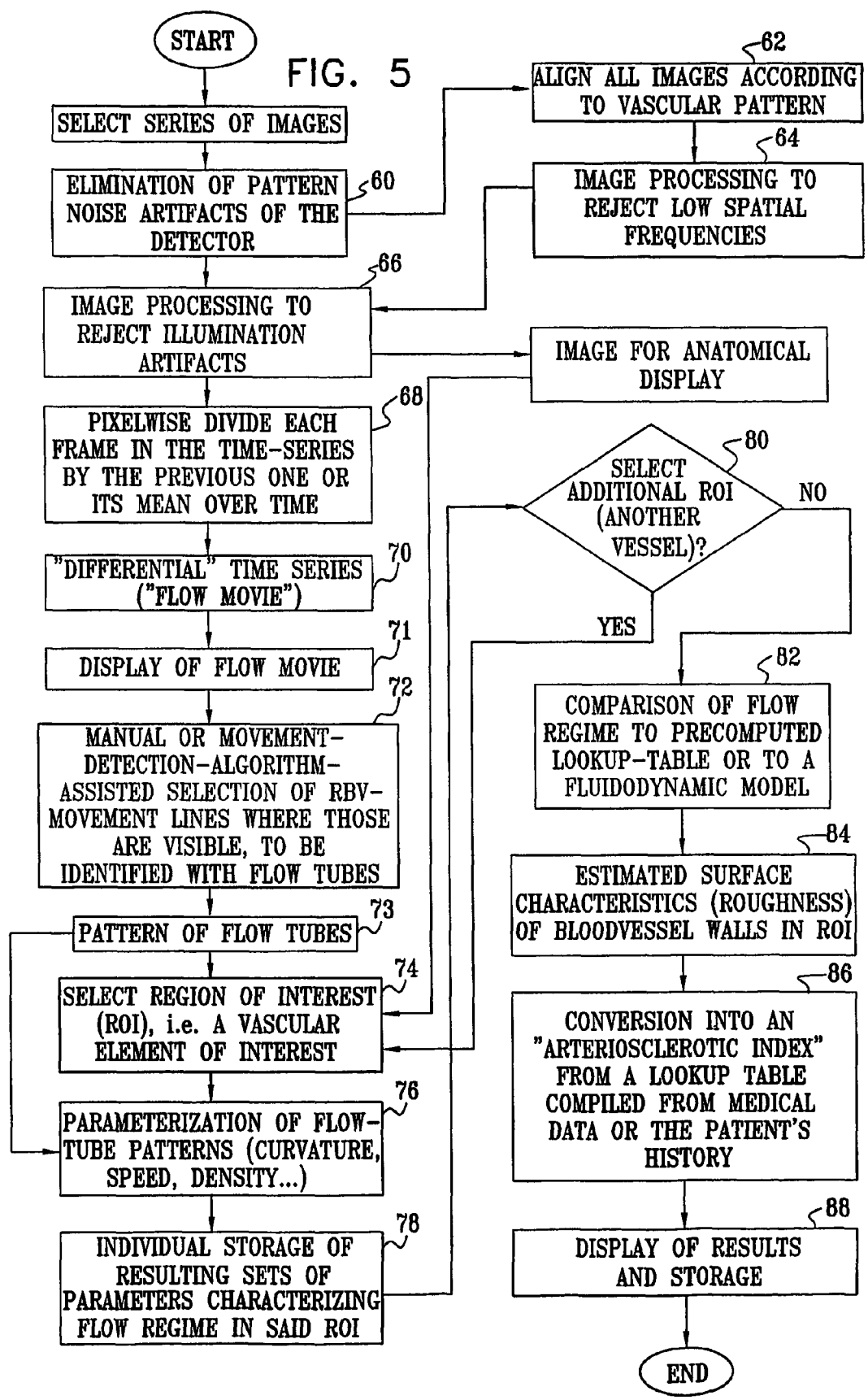

CHARACTERIZATION OF ARTERIOSCLEROSIS BY OPTICAL IMAGING

This application claims the benefit of U.S. Provisional Application No. 60/430,268 filed 2 Dec. 2002 and incorporates the same by reference.

FIELD OF THE INVENTION

The present invention relates to methods for characterizing the level of arteriosclerosis in a subject's vascular system, by means of optical imaging of blood flow at an optically accessible location, especially in the blood vessels of the eye.

BACKGROUND OF THE INVENTION

Adequate blood supply to living tissue is a fundamental prerequisite for its proper functioning. This supply, however, is often impaired due to several acute and/or chronic diseases, for instance, mechanical obstruction or inflammation as a consequence of arteriosclerosis or diabetes. An impaired blood supply can damage tissue locally or systemically, causing generalized pathologies, or pathologies specific to the heart, brain, eye, etc. Many of these diseases are both progressive and treatable, especially if diagnosed in their early stages. Early detection is thus highly desirable, because it enables preventive treatment. The high incidence of pathological vascular alterations in the population, and the severe consequences of their later stages, makes early detection and treatment even more desirable.

Methods for assessing the internal condition of blood vessels should ideally be rapid, objective, quantitative, preferably continuous, and as non-invasive as possible. Most important, there is the need for a test, which can be simply performed as a screening test on a large population, and by personnel with minimal technical training, in a similar fashion to blood-pressure measurements. MRI and non-invasive ultrasound imaging techniques lack the spatial resolution necessary to detect the onset of arteriosclerotic deterioration of blood vessel walls. The current gold-standard for the detection of plaques is autoradiography or scintigraphy, by means of the targeted injection of radioactive substances by a catheter. However, these techniques are invasive, not totally risk-free and very demanding, requiring complicated technical equipment and skilled medical personnel. They cannot, therefore, be performed as a screening test on a large population and are usually reserved for patients already suffering from the consequences of arteriosclerosis. Indirect examination, such as chemical blood analysis for cholesterol, triglycerides, lipids, HDL and other substances can be performed on a large scale, but are only indicative.

Methods assessing the status of blood vessel walls have been described in "MR imaging of the vessel wall", by H. H Quick., J. F. Debatin and M. E. Ladd, published in Eur. Radiol., Vol. 12(4), pp. 889-900 (Apr.2002), and are indicative of the effort invested in developing such techniques. With the exception of endoscopy and MRI, generally used techniques for determining the status of blood vessel walls rely on macroscopic changes, such as an impaired blood exchange rate, leakage, or impaired supply resulting from partial or total obstructions. Endoscopy does allows direct visualization of the interior of blood vessels, but is invasive, not risk-free, and requires skilled medical personnel. MRI, though generally non-invasive, suffers from low signal to noise ratio. Radio frequency (RF) coils have been developed to improve the signal, but some of the most effective of these are for intravascular use, thus rendering the technique invasive. Non-invasive surface coils are limited in application to large vessels near the body's surface—primarily the carotid and right coronary arteries. To detect the early development of plaque and to view it globally rather than locally, intravascular contrast agents on the basis of ultrasmall particles of iron oxide can be used as an MRI marker of macrophage activity within the plaque. Tolerance of the injected substance is not always acceptable, however. In all its modalities, MRI requires expensive apparatus.

The main limitations of the previously described in vivo techniques can be summarized as follows:
(i) they have intrinsically low spatial resolution, or for the case of metabolic indicators, such as blood tests, no spatial information at all;
(ii) they are indirect;
(iii) they are invasive;
(iv) they are limited to specific vessels; and
(v) they require expensive apparatus and/or highly trained technical and medical staff to be performed.

Furthermore, since the effect of disease on blood vessels may be heterogeneous across different compartments, data based on tests of the one-vessel-at-a-time type, as in endoscopy, may miss important diagnostic information which would be available from datasets having the character of an image. Also, due to the generally limited spatial resolution of the aforementioned techniques, arteriosclerosis can usually be detected only at a progressed stage, in the presence of large plaques, whereas early detection is highly desirable.

There thus exists a need for a new method and technique that can quantitatively assess the status of blood vessel walls. The method should preferably be non-invasive, should preferably not necessitate the use of overly expensive and complicated apparatus, and should not require complex know-how or advanced medical proficiency. In addition, the method should be able to assess the state of blood vessel walls for the different vascular compartments, including arteries, arterioles, capillaries, venules and veins, each of which may be affected differently by a given pathology. The method should be capable of detecting small blood vessels non-invasively at high-resolution.

The disclosures of the documents and publications mentioned in this section, and in the other sections of this application, are hereby incorporated by reference, each in its entirety.

SUMMARY OF THE INVENTION

There is therefore provided, in accordance with a preferred embodiment of the present invention, a method and system for detecting abnormalities in the properties of blood vessel walls by observing optical anomalies in the characteristics of blood flow in those vessels, or in connected blood vessels. It is known that progressive morphological alterations of blood vessel walls affect blood flow, changing its spatio-temporal characteristics and ultimately giving rise to pathology due to progressive obstruction or rupture of vessels. The same changes in flow characteristics can be used to detect changes in the properties of the blood vessel walls, even at early stages.

For example, a local reduction in the lumen of a blood vessel gives rise to characteristic spatial patterns in blood flow, which differ from the patterns observed in an unobstructed blood vessel. Such a blood flow pattern can generally be observed by means of the movement of erythrocytes. In particular, the surface structure of the interior of the vessel walls affects these patterns, which can thus be used to differentiate between vessels with smooth inner surfaces and those with "rough" inner surfaces, the "roughness" typically arising from sclerotic plaques or other deposits, or from micro-lesions of the blood vessel. Such information about the surface of the inner walls of blood vessels allows early diagnosis of arteriosclerosis or other related pathologies. Though there are various types of deposit which can form on the inner walls of a subject's blood vessels, the generalized term "plaque" is usually used throughout this application, and is claimed as such, to delineate any type of deposit.

According to another preferred embodiment of the present invention, there is also provided a method for the direct and immediate measurement of the amount and location of plaques on the walls of blood vessels, by means of biochemical or antibody labeling of the arteriosclerotic plaque or part of it, using one or a combination of the techniques of fluorescent, absorptive, reflective or radioactive labeling, followed by fluorescence, or absorption or reflection or radioactivity imaging of the retinal vasculature to detect such labeled arteriosclerotic plaque.

In the case of radioactive imaging, the amount and location of arteriosclerotic plaques can be measured in most parts of the body, due to the high penetration power of the emitted radiation. Markers for various detection methodologies at different wavelengths, conjugated to antibodies of many types, are nowadays being routinely developed using the tools of molecular biology and biological chemistry.

Depending on which part of the body is observed, compromised blood vessel condition causes different symptoms, which can then be used for diagnosing the relevant illness or illnesses, such as arteriosclerosis or arteriothrombosis. At this point, treatment is started for the purpose of impeding further degeneration. In many cases, however, the symptoms which enable the diagnosis to be made only when the vascular alterations are already progressed. In most cases, they are themselves pathological and often irreversible, such as in peripheral arterial occlusive disease, coronary artery disease, cardio- or cerebro-vascular disease in general, stroke, infarction, and the like. It is thus desirable to detect such problems as early as possible, before irreversible damage has occurred. Whereas ideally it would be desirable to have access to the whole vascular system, practically it is generally sufficient to sample only one, or a few representative locations, since the character of such vascular illnesses is in most cases global, rather than local. This has been shown, for instance, in the publication by Dormandy, et al., entitled "Lower-extremity arteriosclerosis as a reflection of a systemic process: implications for concomitant coronary and carotid disease", published in Semin. Vasc. Surg., pp. 118-122, Vol. 12(2), June 1999. Non-invasiveness of the detection method is highly desirable, both for patient convenience and safety. Invasive monitoring of blood vessels is a delicate procedure, since mechanical manipulation of the interior of blood vessels can result in serious and even fatal consequences, even if the blood vessels are not yet heavily compromised. This is described in the article entitled "Fatal lipid embolism following intra-arterial angiography at an early stage of arteriosclerosis" by Kutzner et al., published in British Journal of Radiology, Vol. 73(874), pp. 1108-1111, October 2000. Furthermore, the procedure requires a high level of sterility.

Offering simple optical access to its retinal blood vessels, the eye is a window, through which it is possible to non-invasively sample the state of the vasculature. From this sample, conclusions can be drawn about the state of the vasculature in general, and specifically about the coronary vasculature. Examples of the evidence for links between the vascular condition in the retina, heart and brain are given in the article "Retinal Microvascular Abnormalities and Incident Stroke: the Atherosclerosis Risk in Communities Study" by Wong T. Y., et al., Lancet, 358(9288) pages: 1134-40 (2001); in the article "Retinal arteriolar narrowing and risk of coronary heart disease in men and women. The Atherosclerosis Risk in Communities Study" by T. Y. Wong et al., JAMA; 287(9), pages: 1153-1159, 2002, and in the article "White matter lesions, retinopathy, and incident clinical stroke" by T. Y. Wong et al., JAMA; 288(1); pages 67-74, (2002)

In addition to the retinal vasculature, there are other parts of the body which contain blood vessels close to their surface, and which can be viewed endoscopically, such that the flow in these blood vessels is also readily imaged optically, with minimal risk of complication. Such tissues include the intestinal and the esophageal tissues, though optical access to both is more difficult than to the retinal surface. Furthermore, where relevant or necessary, access can even be provided by minimally invasive means such as laproscopy, to blood vessels near the surface of organs even less generally accessible, such as the brain cortex, or other internal organs.

According to various preferred embodiments of the present invention there are also generally provided methods and systems for measuring, analyzing, and quantifying the status of surfaces which constrain the flow of inhomogeneous fluids. Such inhomogeneous fluids are described as those containing granularly distributed chromophores, and the measurements are performed by using the spatio-temporal patterns of flow, preferably laminar flow, in readily present or easily achievable "windows" into a larger system of "tubes". A preferred application is the assessment of the roughness parameter of the interior surface of blood vessel walls, by characterizing the flow or movement patterns of erythrocytes in blood vessels of the living organs of a body. This is performed by using optical methods for inspection of readily optically accessible blood vessels, such as the retinal vasculature, which is regarded as acting as a window for the entire body vascular system.

Yet another preferred application of the present invention, is the use of fluorescent, reflecting, absorbing and/or radioactive extrinsic markers, to bind specifically to molecular components of arteriosclerotic plaque or other physical alterations of otherwise healthy smooth vessel walls. The optical fluorescence, reflection or absorption imaging of such markers is preferably utilized to map the distributions of the alterations in the vessel walls in the retinal vasculature, which is readily exposed for optical inspection. A preferred application of the use of radioactive or radioactivity-opaque markers bound to the arteriosclerotic plaque is to image the degree of arteriosclerosis in essentially any part of the body, preferably by using computerized tomography, without the need of exposed vasculature, due to the high penetration power of radioactivity.

In the various embodiments of the present invention, the assessment of the nature of laminar flow is generally described using flow in the retinal vasculature to infer the degree of arteriosclerosis in the heart, or in the vascular system in general. It is to be understood though, that the invention is not limited to the retina, but is rather applicable to any other location in the body which allows optical access to blood vessels, such as the intestinal and the esophageal tissues, which are accessible by endoscopic examination, or even tissues in organs only accessible by invasive techniques.

The system is preferably described using an optical imaging system but it is to be understood that it is not limited to optical imaging in the sense of employing visible electromagnetic radiation. The present invention is useful in imaging, analyzing or quantifying the spatio-temporal patterns of blood-flow or erythrocyte movement in retinal blood, or the spatial distribution or quantity of exogenous markers specifically binding to arteriosclerotic plaques, resolved for the different vascular compartments e.g. in capillaries, arterioles, venules, arteries and veins or a subset of those.

Preferred embodiments of the present invention provide a system and method that utilizes the imaging of the flow patterns created by an obstacle rather than the imaging of the obstacle itself. In an overall regime of laminar flow, the fluid flows in flux lines parallel to the surfaces of the walls, and thus the flow patterns reflect the surface geometry. For the case of a tube with smooth surfaces, those patterns are those of laminar flow, i.e. concentric cylindrical laminae of blood flowing at a velocity given by the expression:

$$v(r) = v_m(1 - r^2/R^2),$$

where r is the radial distance from the center and R is the vessel radius, $v(r)$ is the velocity at radius r, and $v_m$ is the velocity at the center, which is also the maximal velocity. A side view of a fluid containing granularly distributed chromophores flowing in such a cylindrically symmetric regime, gives rise to a regular pattern of elongated, tendentially parallel lines of motion of the granules, the speed of which, when moving from the blood vessel walls towards its center, increases according to the above equation, and which is roughly symmetrical with respect to the center line of the tube. On the other hand, protrusions and/or indentations in the surface of the limiting walls show up by more irregular patterns, eventually causing the cylindrical symmetry in the flow patterns to break down if the protrusions or indentations are not themselves cylindrically symmetric. For the preferred example of a blood vessel, sclerotic plaques and obstructions rarely are so. This can happen because the more external flux lines follow the wall profile and its protrusions and/or indentations, thus giving rise to curved flux lines, or because of the appearance of local turbulences.

Those deviations with respect to the classical patterns of laminar flow in a tube can thus be inferred by analysis of flow patterns in the system, measured by any means, whether in a biological or other context, preferably by imaging of the patterns, or by rapid scanning. Quantification is performed preferably by taking into account parameters such as mean curvature of the motion lines, the deviation from cylindrical symmetry, the spatial density of local turbulences or the local deviations from the global character of flow, but other ways of quantification are equally useful.

A preferred mode of operation relies on visualizing flow in individual blood vessels, such as by the methods described in U.S. Pat. No. 6,588,901 for "Imaging and Analyzing Movement of Individual Erythrocytes in Blood Vessels" to A. Grinvald and D. Nelson, or by tracking the movement of individual red blood cells or clusters thereof using scanning strobed or pulsed laser light, preferably in the eye but possibly in any other place in the body. This method uses differential imaging, in which two or more images taken at close time intervals, typically ten to hundreds of milliseconds, are subtracted one from another, or from a mean-over-time image, yielding, respectively, two or more differential images. In this way information arising from the essentially stationary background, such as tissue, muscle or nerve fibers, pigments, etc., is discarded, and only information about objects which have moved during the time interval, is retained. In a vascular network embedded in living tissue, such moving objects could preferably be the erythrocytes flowing within the blood vessels, and a preferred way of detecting a blood vessel comprises analyzing the spatial displacements of the erythrocytes in differential images for line-like patterns, preferably using standard imaging processing tools.

With perhaps the exception of the large, high-pressure vessels such as the aorta, if the limiting blood vessel walls are smooth, as in a healthy organism, blood generally flows in a laminar regime, thus creating regular, elongated patterns of moving erythrocytes, marking the flux-tubes. If however, the inner surfaces of the blood vessel walls are rough, due for instance to the presence of arteriosclerotic plaques, the flux lines become irregular close to the blood vessel walls, since they follow the rough contour of the walls. Particularly pronounced isolated protrusions from the blood vessel wall's inner surface, or partial occlusions may even give rise to turbulence, showing up in patterns of erythrocyte motion which clearly differ from those characterizing laminar flow. Use can then be made of the line density of those irregularities as well as the amount of deviation of the flux lines near the vessel wall from straight lines, preferably by an average curvature parameter or by the distribution of the flux lines' curvatures, to quantify the roughness of the blood vessel walls. Such a measure can be performed even if the flow characteristics are known only partially, such as only in the proximity of the walls, which may be the case for imaging performed through the walls.

As described hereinabove, the outlined method consists of three distinct steps:
(i) the identification of the flow patterns, preferably by imaging a system of motion lines of erythrocytes or any other uniformly but granularly distributed chromophores;
(ii) the assessment of their deviation from elongated, low-curvature flux lines characteristic of the laminar flow generated close to smooth delimiting walls; and
(iii) the inference of the "status" of the delimiting walls of the fluid flow system from the aforementioned characteristics of flow, in particular, whether the walls are smooth or rough.

As described hereinabove, alternatively and preferably, the amount and location of plaques on the walls of blood vessels can be assessed by means of optical fluorescent, reflective, or absorptive biochemical or antibody-labeling of the arteriosclerotic plaque, followed by optical imaging of the retinal vasculature to detect such labeled arteriosclerotic plaque.

Alternatively and preferably, the amount and location of plaques on the walls of blood vessels can be assessed by means of radioactive or radiation-opaque biochemical or antibody-labeling of the arteriosclerotic plaque followed by radiation imaging of nearly every other part of the body.

According to a further preferred embodiment of the present invention, use is made of the generally accepted principle in medical practice, that "the eye presents a good window for what is happening in other parts of the body". For the purposes of this additional embodiment, use is made of the supposition that the retinal tissue often reflects the state of the tissues of other organs situated elsewhere in the body. Thus, if the subject is treated so as to generate a molecular label which provides an optically detectable indication of a pathological condition relating to a certain disease, and the effects of that molecular label are detectable in the retinal tissue, that presence, or more specifically the optical characteristics thereof, should provide information also about the presence of the condition in another organ which otherwise would only be accessible invasively. In this way, it is possible, as an example, to rapidly detect an optical effect such as the fluorescence arising from labeled pathogenic matter in the retinal tissue, which may be common to that of a disease present in another, inaccessible organ, such as the liver. Such fluorescence measurements need not be limited to intensity only, but could also be of the fluorescence decay time, polarization, wavelength shift or any other known parameter characterizing the fluorescence, or other optical properties of the label used for the test.

There is thus provided, in accordance with a preferred embodiment of the present invention, a method for vascular analysis of a subject, comprising the steps of optically imaging at least one optically accessible blood vessel of a subject, determining from the optical imaging at least one flow characteristic of erythrocytes in the at least one optically accessible blood vessel, and utilizing the at least one flow characteristic for determining the roughness on the inner wall of the at least one optically accessible blood vessel. The at least one optically accessible blood vessel may preferably be a retinal blood vessel, in which case the method is performed non-invasively, or it may be located in the tissue of an internal organ. This tissue may preferably be esophageal, gastrointestinal, or brain tissue, or the internal surface of a passageway.

In the above-described method, the optical imaging step preferably comprises acquiring at least two sequential images of erythrocytes in the at least one optically accessible blood vessel. Alternatively and preferably, the method also comprises the step of utilizing the determination of the roughness on the inner wall of the at least one optically accessible blood vessel in order to ascertain the condition of another blood vessel of the subject, and preferably to ascertain the level of arteriosclerosis in the subject.

In accordance with still another preferred embodiment of the present invention, the at least one flow characteristic of the erythrocytes comprises at least one of the mean curvature of the motion lines of the erythrocytes, the deviation from cylindrical symmetry of the motion lines of the erythrocytes, the spatial density of local turbulences in the motion lines of the erythrocytes, and the local deviations from the global character of the motion lines of the erythrocytes.

There is further provided in accordance with still another preferred embodiment of the present invention, a method for vascular analysis of a subject, comprising the steps of:
(i) optically imaging at least one optically accessible blood vessel of a subject having a first blood pressure, the blood pressure being subject to change,
(ii) optically imaging the at least one optically accessible blood vessel again when the blood pressure of the subject has changed to a second value,
(iii) determining from the optical imaging of steps (i) and (ii) at least one flow characteristic of erythrocytes in the at least one optically accessible blood vessel, at the first and the second blood pressure, and
(iv) utilizing differences obtained in the at least one flow characteristic at the first and the second blood pressure to determine a roughness index of the inner wall of the at least one optically accessible blood vessel.

In this above described method, the change of the first blood pressure to the second blood pressure may preferably be caused by either drugs administered to the subject or by exercise. Alternatively and preferably, the change of the first blood pressure to the second blood pressure may be a result of the subject's heartbeat. In such a case, the method also preferably comprises the additional step of synchronizing the optically imaging steps to the subject's heartbeat. Such synchronizing is preferably performed by monitoring at least one of the subject's heartbeat cycle and blood pressure, and using the monitoring to control the timing of the optical imaging.

In accordance with a further preferred embodiment of the present invention, there is also provided a method for detecting arteriosclerotic plaque on the walls of blood vessels of a subject, comprising the steps of providing a biochemical label for the plaque having predetermined optical properties, labeling of at least part of the arteriosclerotic plaque with the biochemical label, and optically imaging at least one optically accessible blood vessel to detect the labeled arteriosclerotic plaque. In this method, the at least one optically accessible blood vessel of the subject may preferably be a retinal blood vessel, an esophageal blood vessel, or an intestinal blood vessel. Furthermore, in this method, the predetermined optical properties of the biochemical label may preferably be at least one of fluorescent, absorptive and reflective properties, and the optical imaging is then accordingly at least one of fluorescence, absorption and reflection imaging. The biochemical label may preferably be an antibody label.

There is also provided in accordance with yet a further preferred embodiment of the present invention, a method for detecting arteriosclerotic plaque on the walls of blood vessels of a subject, comprising the steps of providing a radioactive biochemical label for the arteriosclerotic plaque, labeling of at least part of the arteriosclerotic plaque with the radioactive biochemical label, and radiographically imaging at least one of the blood vessels of the subject to detect the radioactively-labeled arteriosclerotic plaque. In this method, the at least one of the blood vessels of the subject may preferably not be optically accessible. Furthermore, the biochemical label may preferably be an antibody label.

In accordance with yet more preferred embodiments of the present invention, there is provided a system for vascular analysis of a subject, comprising:
(i) a light source for illuminating at least one optically accessible blood vessel of the subject,
(ii) an imager for acquiring a plurality of images showing sequential spatial distribution of moving erythrocytes in the at least one optically accessible blood vessel,
(iii) an image discriminator determining from the plurality of images showing sequential spatial distribution, a flow pattern of erythrocytes along the blood vessel,
(iv) a flow analyzer analyzing the flow pattern to determine at least one flow characteristic of erythrocytes along the at least one optically accessible blood vessel of the subject, and
(v) a wall analyzer utilizing the at least one flow characteristic for determining at least one property of the inner surface of the blood vessel.

In the above-described system, the at least one property of the inner surface of the blood vessel may preferably be the roughness of the inner surface of the blood vessel. The system may also preferably comprise an arteriosclerotic index determiner utilizing the roughness to determine the level of arteriosclerosis in the at least one optically accessible blood vessel. This arteriosclerotic index determiner may preferably utilize the roughness to ascertain the arteriosclerotic condition of another blood vessel of the subject.

In any of the above-described systems, according to another preferred embodiment of the present invention, the at least one flow characteristic of the erythrocytes preferably comprises at least one of the mean curvature of the motion lines of the erythrocytes, the deviation from cylindrical symmetry of the motion lines of the erythrocytes, the spatial density of local turbulences in the motion lines of the erythrocytes, and the local deviations from the global character of the motion lines of the erythrocytes. The system also preferably comprises a wavelength selecting device, such that the imager acquires the images of the at least one optically accessible blood vessel over a limited wavelength band. This wavelength selector is preferably located either in the illuminating pathway between the light source and the at least one optically accessible blood vessel, or in the imaging pathway between the at least one optically accessible blood vessel and the imager. The limited wavelength band of the wavelength selector is preferably between 2 and 30 nanometers.

In accordance with yet another preferred embodiment of the present invention, the light source for illuminating the at least one optically accessible blood vessel of the subject imager is preferably a pulsed source having a pulse to pulse interval of less than 1 second, or more preferably, between 5 and 200 milliseconds, or even more preferably between 5 and 40 milliseconds.

Alternatively and preferably, in the above-mentioned systems, the light source for illuminating the at least one optically accessible blood vessel of the subject imager is a continuous source, and the imager acquires images at predetermined intervals.

Furthermore, in any of the above-mentioned systems, the at least one optically accessible blood vessel of the subject is a retinal blood vessel or is located in tissue of an internal organ. This tissue may preferably be either esophageal, gastro-intestinal or brain tissue, or the internal surface of a passageway.

In accordance with still another preferred embodiment of the present invention, there is provided a system for vascular analysis of a subject, comprising:
(i) a light source for illuminating at least one optically accessible blood vessel of the subject, after ingestion by the subject of a biochemical label which labels arteriosclerotic plaque such that it has predetermined optical properties,
(ii) an optical imager for acquiring at least one image of the at least one optically accessible blood vessel of the subject,
(iii) an image processor utilizing the acquired at least one image of the at least one optically accessible blood vessel of the subject to determine the amount and location of regions of the predetermined optical properties of the labeled arteriosclerotic plaque, and
(iv) a mapper to generate a map of the arteriosclerotic deposits in the walls of the at least one optically accessible blood vessel of the subject.

In the above-described system, the predetermined optical properties of the biochemical label are at least one of fluorescent, absorptive and reflective properties, and the at least one image is then accordingly at least one of a fluorescence, absorption and reflection image. Furthermore, the map of the arteriosclerotic deposits in the walls of the at least one optically accessible blood vessel of the subject may preferably be utilized to ascertain the arteriosclerotic condition of another blood vessel of the subject. The biochemical label may be, according to a further preferred embodiment, an antibody label.

There is even further provided in accordance with a preferred embodiment of the present invention a system for vascular analysis of a subject, comprising a radiographic apparatus for imaging the subject after ingestion by the subject of a predetermined dose of a radioactive biochemical label for arteriosclerotic plaque, and a plaque location deriver utilizing at least one image provided by the radiographic apparatus to determine the location of the radioactive biochemical label, wherein the location of the radioactive biochemical label is utilized to determine the presence of arteriosclerotic plaque on the walls of at least one blood vessel of the subject. The at least one blood vessel of the subject may preferably be not optically accessible, and the biochemical label may preferably be an antibody label.

BRIEF DESCRIPTION OF THE DRAWINGS

The present invention will be understood and appreciated more fully from the following detailed description, taken in conjunction with the drawings in which:

FIG. 4 is a schematic flowchart illustrating the steps taken, according to preferred methods of the present invention, for acquiring image data of the area of interest to be analyzed for flow abnormalities;

FIG. 5 is a schematic flowchart illustrating the steps taken, according to a preferred method of the present invention, for analyzing and displaying the data obtained by the method of the flowchart of FIG. 4, and for determining the arteriosclerotic state of the blood vessels of the subject under examination;

DETAILED DESCRIPTION OF PREFERRED EMBODIMENTS

With specific reference now to the figures in detail, it is stressed that the particulars shown are by way of example and for purposes of illustrative discussion of the preferred embodiments of the present invention only, and are presented for the purpose of providing what is believed to be the most useful and readily understood description of the principles and conceptual aspects of the invention. In this regard, no attempt is made to show structural details of the invention in more detail than is necessary for a fundamental understanding of the invention, the description taken with the drawings, making it apparent to those skilled in the art how the several forms of the invention may be embodied in practice.

Reference is now made to FIG. 1, which is a schematic block diagram illustrating a system, according to a preferred embodiment of the present invention, for non-invasively measuring the properties of the inner surface of blood vessels, by means of imaging the erythrocyte flow in the retinal vasculature. The system has some elements similar to that described in the above-mentioned U.S. Pat. No. 6,588,901, where the apparatus is used to determine the flow velocity of the RBC's, and/or their direction of motion, and to that described in co-pending PCT Application No. PCT/IL03/00275 for "Characterization of Moving Objects in a Stationary Background", to the inventors of the present invention, in which the apparatus is used to non-invasively measure oxygen saturation in blood vessels, by spectrally decomposing the separated spectrum of the moving red blood cells, especially as applied to blood vessels which do not show significant pulsation Both of these patent documents are hereby incorporated by reference, each in its entirety.

Figure 1A:
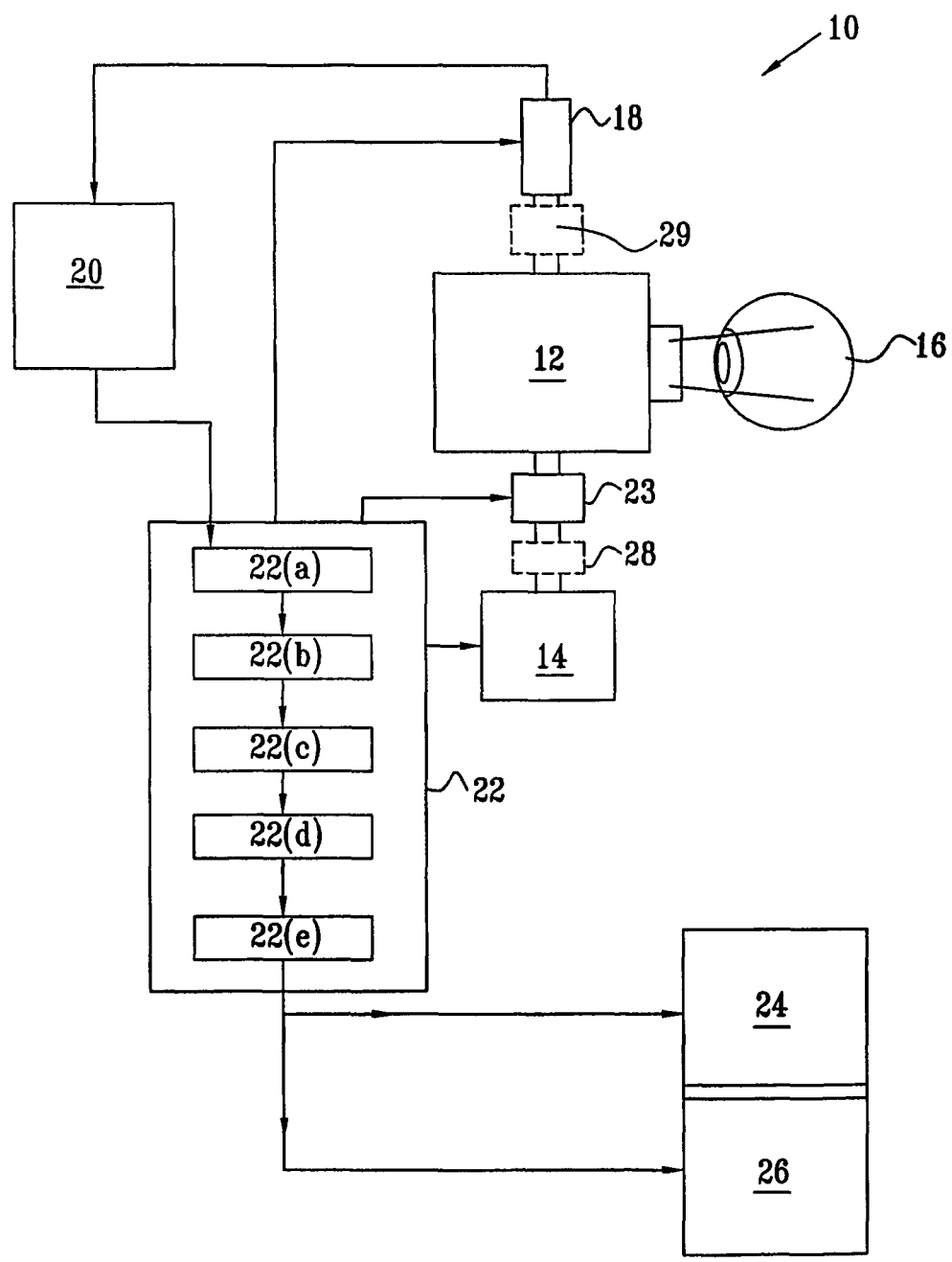
FIG. 1A is a schematic block diagram illustrating a system according to a preferred embodiment of the present invention, for non-invasively measuring the properties of the inner surface of blood vessels, by means of imaging the erythrocyte flow in the retinal vasculature.

In the preferred embodiment shown in FIG. 1A, the system 10 is shown performing the measurements on the blood vessels in a retina, but it is to be understood that the system is equally useful for application to the blood vessels in other accessible organs, such as by using an endoscopic or laproscopic probe for illuminating and imaging the surface tissues of optically accessible internal organs, such as the esophagus or the surface tissue of the brain.

The system 10 of FIG. 1A comprises an imaging optics arrangement 12, for imaging the surface layers of the organ of interest. For imaging the retina 16, the imaging optics arrangement 12, is preferably a fundus camera or an ophthalmoscope. For imaging other internal organs, the imaging optics arrangement can preferably include a high quality objective head, or a macro-camera lens, and can preferably include an optical endoscopic or laproscopic probe for imaging organs generally inaccessible from outside the body. Such an arrangement is shown schematically in FIG. 1B which shows a preferred imaging optics arrangement including a fiber optical probe 30 in use for imaging the surface of a subject's esophagus, as an example of the inspection of a generally inaccessible internal organ. Likewise, the system 10 can also be used, according to further preferred embodiments of the present invention, for the analysis of the flow in paths other than blood vessels in the tissues of a subject, by the use, inter alia, of suitably adapted imaging optics and data processing modules.

The imaging optics arrangement 12 preferably contains a beam splitting device, a mirror with a central transmission aperture, or another optical arrangement, such that the input illumination, in the presently described embodiment, coming from a flash lamp 14 emitting pulses of light, can be directed towards the illuminated organ tissue 16, along the same optical path as that used by the image information obtained by reflection or scatter from the illuminated tissue of interest 16. Besides a flash lamp 14, any other suitable pulsed illuminating source may also preferably be used, such as a strobed laser or a pulsed laser. The imaging information is preferably received by a high resolution imaging device, such as a CCD camera 18. The output image data from this camera 18 is preferably input to a image acquisition device 20, such as a digital frame grabber, whose timing is preferably controlled by a computing and control system 22, which also preferably processes the image output data. The computing and control system 22 also preferably controls the timing of the flash lamp or pulsed source 14, when used, or of the other preferred source. The requirement of a pulsed source is generally mandated for retinal imaging, since there is need to limit the light flux incident on the retina, and pulsing or flashing is the best way to input sufficient illumination in a short time frame. For the imaging of other tissues, such as esophageal tissue, the source can preferably be continuous, and the sequential images can be obtained by gating or frame grabbing of the camera images. Since retinal blood vessels are the simplest to access optically, the remainder of this application is described in terms of embodiments using a pulsed source, though it is to be understood that the methods and systems described herein, with the exception of the obvious differences necessitated by the changed configuration, are also applicable to continuous sources and gated imaging.

The computing and control system 22 preferably comprises a number of internal modules for performing specific computing and control steps, such as:

(a) an imager and processor 22a for obtaining clear and stationary images in blood vessels in the region being imaged;

(b) an image feature discriminator 22b for image sequence comparison to determine changes from image to image;

(c) a flow analyzer 22c for characterizing the flow regime in the vessels in the region being imaging, preferably comprising a flow-line parameterization assigner utilizing the changes from image to image to determine at least one flow characteristic of erythrocytes in a blood vessel being imaged; and (d) a wall analyzer 22d, utilizing the flow characteristic output from the flow analyzer for determining the properties of the inner wall of the blood vessel, and especially the inner wall roughness.

Additionally and preferably, the computing and control system 22 also comprises an arteriosclerotic index determiner 22e, using the blood vessel internal surface roughness to determine the level of arteriosclerosis in the blood vessel being imaged. Additionally, the arteriosclerotic index determiner may preferably utilize the roughness in order to ascertain the arteriosclerotic condition of blood vessels elsewhere in the subject's body, as explained hereinabove.

It is to be understood that the above-described modules used for the analysis within the computing and control system 22, are only one preferred combination for executing the necessary vascular analysis of the present application, and that other combinations which achieve the desired vascular analysis can also be used for executing the present invention.

After generation of this output data, they are preferably directed to a display monitor 24 and/or a printer 26. The operation of each of the component modules of the computing and control system 22 will be more fully explained hereinbelow with reference to the flow charts of FIGS. 4 to 6. The system may also preferably include a component arrangement for calibrating the illuminating flash, both for spatial variations and for overall intensity variations, as for instance described in the above-mentioned U.S. Pat. No. 6,588,901. Such an arrangement is only necessary if the uniformity of the illuminating source is insufficient, or if the intensity varies significantly from flash to flash.

According to preferred embodiments of the present invention, a wavelength selecting device 28 or 29, may preferably be added to the path of the illuminating beam or the imaged beam, such that a limited or narrow band of incident illumination or of collected light from the retina is used for imaging the blood vessels in the retina. The typically used bandwidth is 2 to 30 nm. These wavelength selecting elements may be bandpass filters as mentioned in the system described in U.S. Pat. No. 6,588,901, in order to provide a bandwidth of light which improves the contrast of the image of the erythrocytes. Since the erythrocytes absorb strongly in the blue and green areas of the spectrum, the filter provides contrast for the erythrocytes with the relatively reflective retina against which they are imaged, and which also contains a large number of pigments of differing colors.

In general, the above-described system is preferably used in order to detect blood flow patterns next to the walls of large blood vessels in the retina through reflection measurements through the walls of said vessels. The imaging optics arrangement 12 can then be a modified fundus camera. The movement of individual red blood cells (RBC's) or conglomerates thereof in individual blood vessels is performed as described in detail in the above-referenced patent documents, preferably using pulses of green light flashed at rapid succession into the eye so as to obtain a "movie" of the movements of the RBCs in the retina. The inter-flash interval is generally less than 1 sec, and typically in the range of 5 to 200 ms, and even more typically, in the range of 5 to 40 ms.

Alternatively and preferably to the illumination of the inner eye by means of full field flashes and the use of an imaging device for imaging the light reflected from the retina with respect to each flash, according to another preferred method of illumination, scanned laser pulses, generated by an optional scanning device 23, can be used, preferably in the green where the absorption of hemoglobin is large, and an imaging detector, such as a 2-dimensional CCD-array employed. Alternatively and preferably, a single detector using precise coincidence timing with the scanning pulses may be used.

The flow patterns showing up along the walls of large vessels in the retina, such as those emerging from the optical disk, are analyzed, preferably to derive parameters or characteristics describing the deviation of the flow from low-curvature lines parallel to the axis of the blood vessel. From those parameters or characteristics, conclusions can be drawn about the roughness properties of the inner surface of the vessels, preferably by comparison to experimentally derived values obtained in a model, by the evaluation of the curvature distributions of flux lines next to the vessel walls, or by using other parameters yielded by theoretical models derived from fluid dynamics.

Furthermore, perturbation of the blood pressure, for example by the use of drugs or exercise, can provide two sets of measurements. A comparison of the value of the derived parameters or characteristics from these two sets, may be used to obtain an index for the roughness of the blood vessels, such as for instance, if the amount of local turbulence, which can be quantified by standard fluid-dynamic tools or by results obtained from a model, is significantly different at the two pressures.

Such perturbation also exists naturally as a result of the heartbeat of the subject, the blood pressure changing cyclically during each heartbeat. According to a further preferred embodiment of the present invention, the imaging of the optically accessible blood vessel is synchronized to predetermined points in time of the heartbeat when the blood pressure is known to be different, and the flow characteristics at these two points in time are compared to obtain an index for the roughness of the blood vessels.

According to yet another preferred embodiment of the present invention, fluorescent, reflective, absorptive or radioactive labeled antibodies, reactive for proteins specifically present in the arteriosclerotic plaque, can be used to label the arteriosclerotic deposits on the blood vessel walls in-vivo, such that they possess the desired fluorescent, reflective, absorptive or radioactive properties. Such labeled antibodies may be developed by molecular biology or biological chemistry, as is known in the art.

Preferred variations of the apparatus shown in FIG. 1A may then be used to obtain optical images of the fluorescence, reflection, or absorption of the retinal vasculature at various magnifications ranging from the visualization of individual vessel segments up to the whole optically accessible retinal vasculature. In particular, the computing and control system will preferably incorporate modules having different functions from those, 22(a) to 22(e), used in arteriosclerotic characterization based on blood vessel flow line measurement. Quantitative analysis of these images then provides a direct measure of the arteriosclerotic level of the vasculature in the eye, which itself is indicative of the situation in the rest of the body, such as the heart.

Further preferred variations of the apparatus shown in FIG. 1A may also be used to obtain optical images of the fluorescence, reflection, or absorption of the retinal tissue, in order to mirror pathological effects present in the tissue of other inaccessible organs of the body.

Figure 1B:
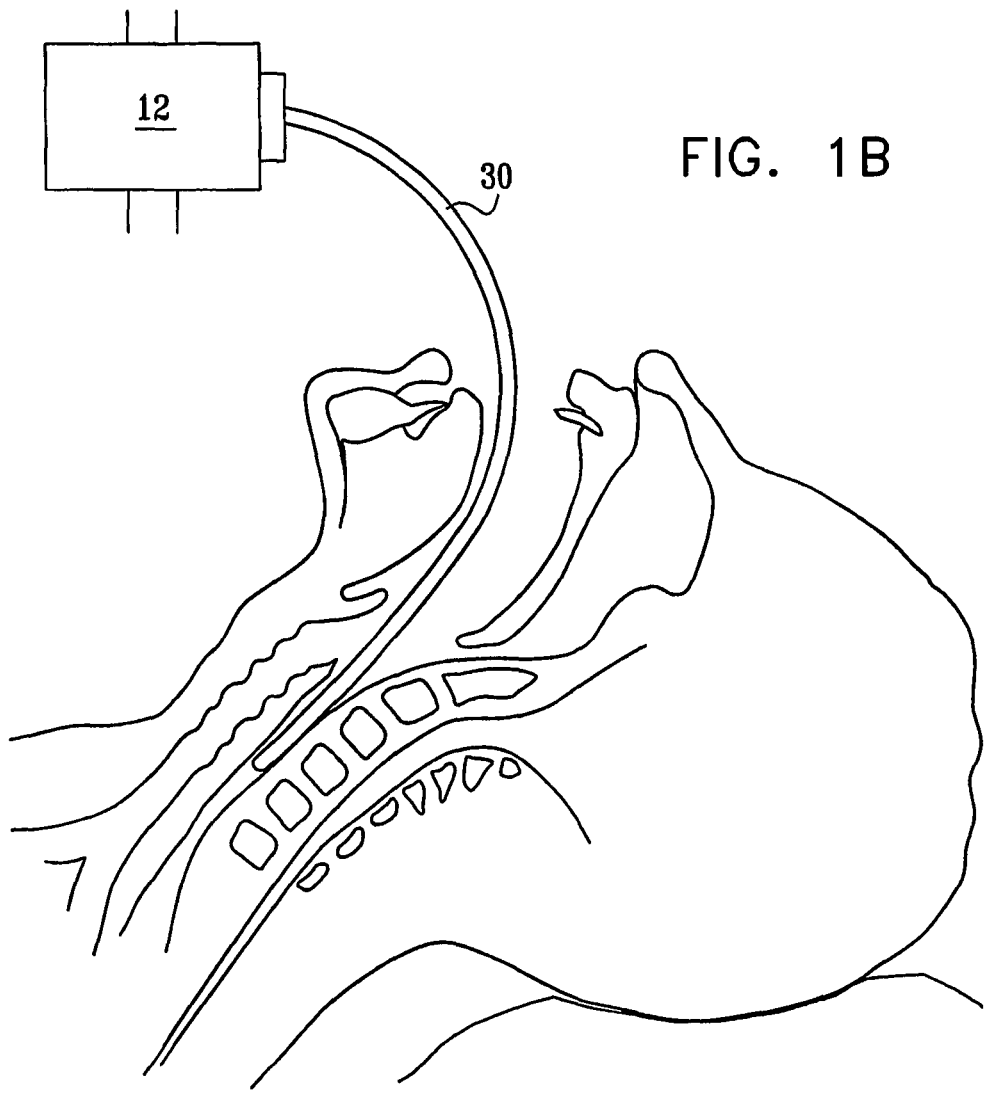
FIG. 1B is a drawing showing a preferred embodiment of the imaging optics arrangement of FIG. 1A, but using a fiber optical probe for imaging the surface of a generally inaccessible organ of a subject.

The same preferred variations of the apparatus shown in FIG. 1A may also be made to the apparatus such as that shown in FIG. 1B, to obtain optical images of the fluorescence, reflection, or absorption of the vasculature or tissues in other accessible parts of the body.

Figure 7:
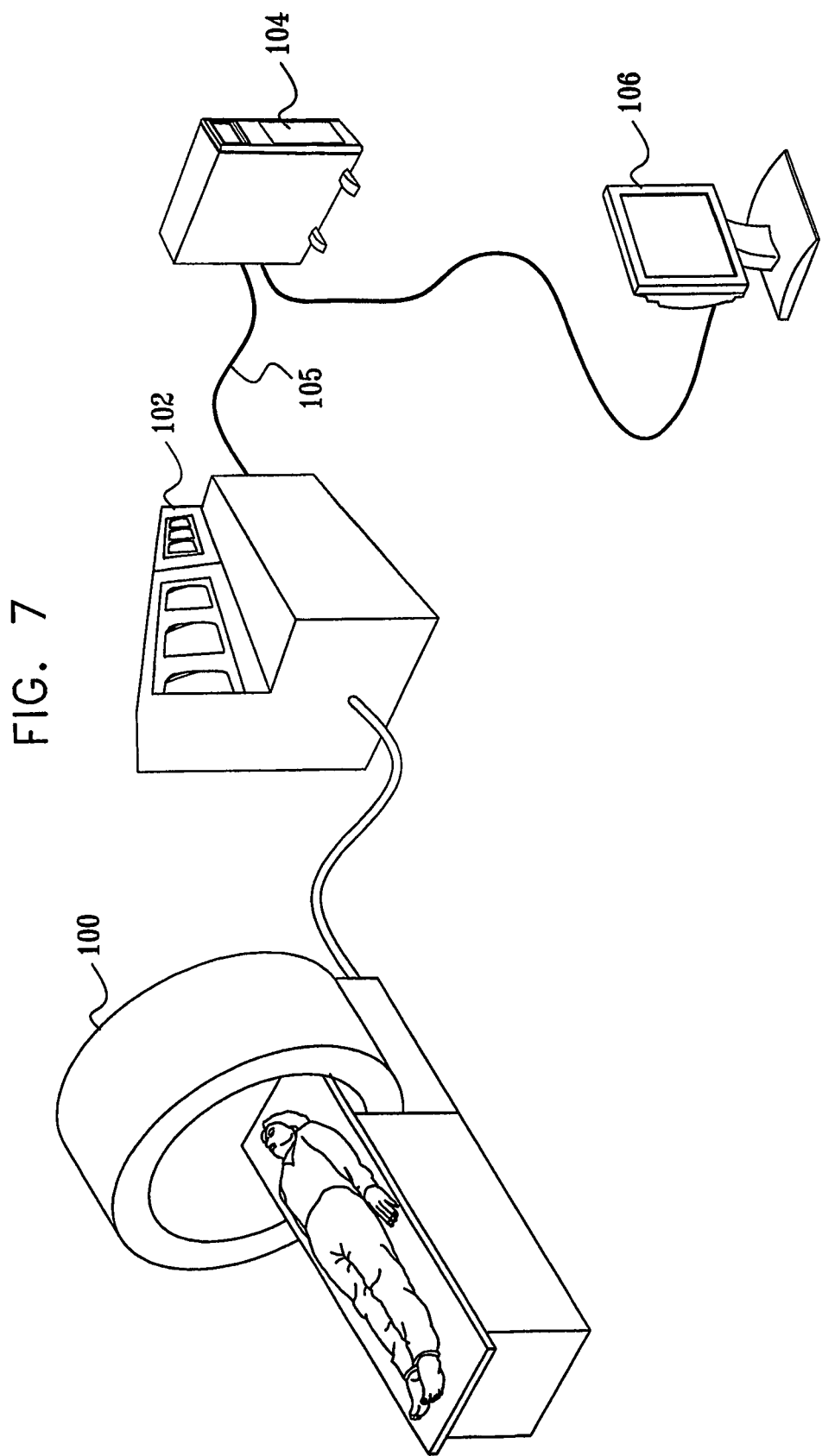
FIG. 7 illustrates a schematic representation of a CT apparatus suitable for the assessment of arteriosclerosis by the imaging of the vasculature anywhere in the body, after labeling of the arteriosclerotic plaque with an exogenous radioactive marker.

In the case of radioactive or radioactivity-opaque markers, the apparatus of FIG. 1A or 1B would not be used, but the radioactivity or opacity could preferably be imaged by means of computerized tomography, and, due to the high penetration power of radioactivity, even in areas of the body where the vasculature is not directly accessible. The degree of arteriosclerosis can thus be determined directly in many parts of the body. FIG. 7, to be described hereinbelow, illustrates a schematic representation of an apparatus suitable for performing such measurements.

Figure 2A:
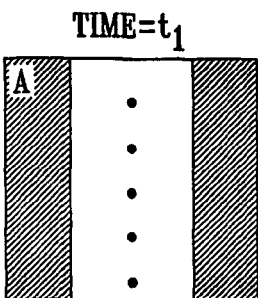
FIGS. 2A to 2E are a series of schematic drawings showing representations of how the spatial pattern of erythrocytes changes in time with motion of the erythrocyte down a blood vessel, and how the motion information can be used to determine the outline of flux lines within the blood vessel.
Figure 2B:
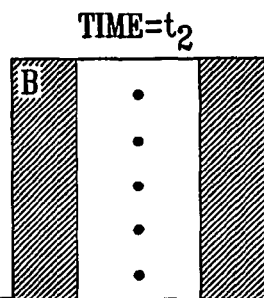
Figure 2C:
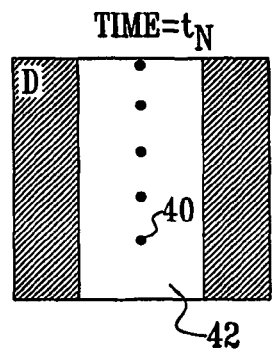

Reference is now made to FIGS. 2A to 2E, which are a series of schematic drawings showing representations of how the spatial pattern of erythrocytes changes in time with motion of the erythrocytes down a blood vessel, and methods, according to other preferred embodiments of the present invention, of separating the motion information from the static information, to provide an outline of flux lines in the blood vessel. Due to the blood flow, erythrocytes or clusters of erythrocytes move, as shown in FIGS. 2A to 2C taken respectively at times $t_1$, $t_2$ and $t_n$, as black dots 40 in a blood vessel segment, 42, shown as a white cross section. The erythrocytes are depicted as black dots, since their absorption in the green spectrum is much larger than that of the surrounding plasma. Different spatial erythrocyte line patterns are seen in the same blood vessel segment at different times $t_1$, $t_2$ and $t_N$. The erythrocytes are moving upwards in the blood vessel.

Figure 2D:
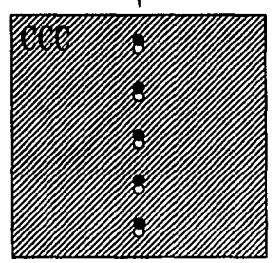
Figure 2E:
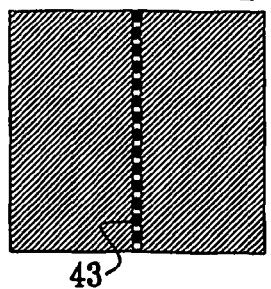

FIG. 2D is a difference image, obtained by subtracting (or in practice, by dividing) the image obtained in FIG. 2B from that of FIG. 2A, and amplifying the result by multiplication by a user-selectable factor. In FIG. 2D, the black dots represent the positions of erythrocytes at $t=t_2$, and the white dots represent the positions of the same erythrocytes a short time before, at $t=t_1$. Many such images can be acquired for a longer time, as shown up to time $t_N$ in FIG. 2C, and on summation with alternating signs, they yield the black-and-white dotted outlines 43 of the flux lines in the flowing blood, as shown in FIG. 2E. An alternative but equivalent approach is to divide each individual image obtained, by the average obtained over all of the frames (FIGS. 2A . . . 2C).

Figure 3A:
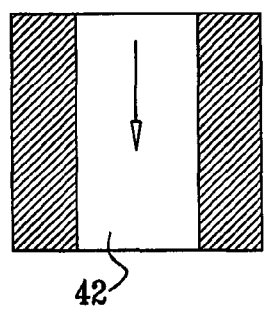
FIGS. 3A to 3F are a sequence of schematic drawings showing images of the flow lines of the erythrocytes in a retinal blood vessel, characterizing the observed flow in a healthy, a partially and a heavily arteriosclerotic vessel.
Figure 3D:
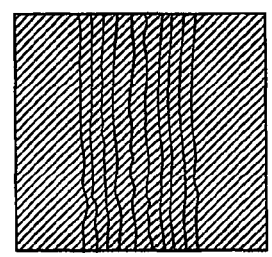
Figure 3B:
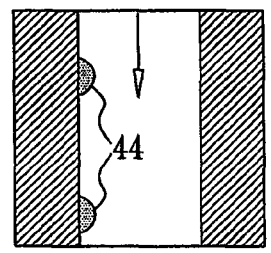
Figure 3E:
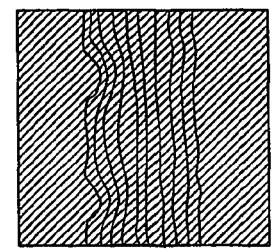
Figure 3C:
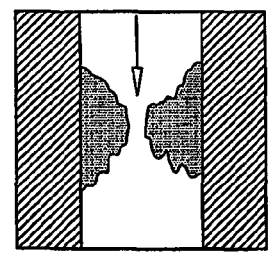
Figure 3F:
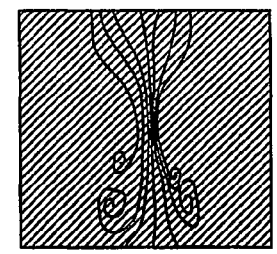

Reference is now made to FIGS. 3A to 3F, which are a series of schematic representations of flow tube patterns characterizing flow in a healthy, partially and heavily arteriosclerotic blood vessel. On the left side of the drawings, in FIGS. 3A to 3C, are schematically shown the morphological appearance of a longitudinal blood vessel section 42, while on the right side of the drawings, in FIGS. 3D to 3F are schematically shown corresponding flow patterns, with the flow direction being from top to bottom in each blood vessel section. In the top row, in FIG. 3A is shown a healthy blood vessel, and in FIG. 3D, the corresponding flow patterns obtained therein, which are cylindrically symmetric around the axis of the blood vessel, and are essentially completely laminar. In the middle row, in FIG. 3B is shown a partially arteriosclerotic vessel with two arteriosclerotic plaques 44 shown on the left side of the blood vessel, and in FIG. 3E, the corresponding flow patterns, showing a generally laminar flow but with some asymmetric disturbance near the plaque deposits. In the bottom row, in FIG. 3C is shown a heavily plaqued blood vessel, nearly occluded by the plaque, and in FIG. 3F are shown the corresponding flow patterns expected, having regions of severely turbulent flow.

Reference is now made to FIG. 4, which is a schematic flowchart illustrating the steps taken, according to preferred methods of the present invention, for acquiring the image data of the area of interest to be analyzed for flow abnormalities. The main steps are as follows:

Step 50. Background image taken (with no illumination).
Step 52. Flash or laser scan to image the area of interest.
Step 54. Storage of image.
Step 56. Fast repetition of steps 52 to 54, preferably at intervals within the range of 5 to 200 milliseconds, and more preferably at intervals within the range of 5 to 40 milliseconds, m times, where m is the number of flashes or laser scans required to get a clear motion signal, and preferably approximately 6 to 8 flashes or scans.
Step 58. Time series of m images is obtained and stored for processing.

Reference is now made to FIG. 5, which is a schematic flowchart illustrating the steps taken, according to a preferred method of the present invention, within the image processor and discriminator modules of the computing and control unit of the system of FIG. 1A, for analyzing and displaying the data obtained in the image sequences obtained by the method of the flowchart of FIG. 4, and for determining therefrom the arteriosclerotic state of the blood vessels of the subject under examination. The main steps are as follows:

Step 60. Elimination of pattern noise artifacts of the detector, performed on the m-timepoint series of images obtained at the output of the data acquisition processes shown in FIG. 4, and using data from step 1 in FIG. 4.
Step 62. Alignment of all images according to the vascular patterns on the retina, performed to eliminate the effect of eye motion during the measurement.
Step 64. Image processing, preferably high-pass filtering of the images, to reject information with spatial frequency significantly lower than that of the retinal vasculature.
Step 66. Elimination of possible illumination artifacts.
Step 68. Dividing each frame in the time series, pixel-by-pixel, by the previous frame or by the mean over time of all of the frames.
Steps 70-71. Creation of a "differential time series (flow movie)" and display thereof.
Steps 72-73. Manual or computer-assisted (by means of available movement detection algorithms) selection of erythrocyte motion lines where visible, to define the flow lines in the imaged blood vessel.
Step 74. Manual selection by the physician of a "region of interest" (ROI), i.e. the relevant vascular element from one of the images obtained after step 66.
Step 76. Parameterization of the flow-tube patterns thus obtained in terms of the curvature, speed of flow, density of the flow, etc.
Step 78. Storage of the resulting sets of flow parameters for the ROI chosen.
Step 80. Repetition of steps 74 to 78 to select different vascular elements, with separate storage of the resulting sets of flow parameters for the ROI's chosen, as many times as desired by the user.
Step 82. Comparison of the flow regime determined, with a precomputed look-up table or with a fluid-dynamics model.
Step 84. Estimation of the surface characteristics (roughness) of the walls of the blood vessel wall in the ROI.
Step 86. Conversion of the surface characteristics into an "arteriosclerotic index" from a look-up table compiled from known medical data or from the patient's history.
Step 88. Display of results, and storage as a medical record.

Furthermore, in addition to the above-described steps of the flow chart of FIG. 5, an extrapolation can then be made of the results obtained for the vasculature under examination, to estimate the general level of arteriosclerosis in other parts of the body.

It is also to be emphasized, that the described algorithms in FIGS. 4 and 5, and that to be described in FIG. 6 below, are only one preferred method by which the relevant data is processed and extracted, and that other methods known in the art can equally well be utilized, if they provide the necessary data analysis procedures for determining the level of arteriosclerosis in the regions under inspection.

Figure 6:
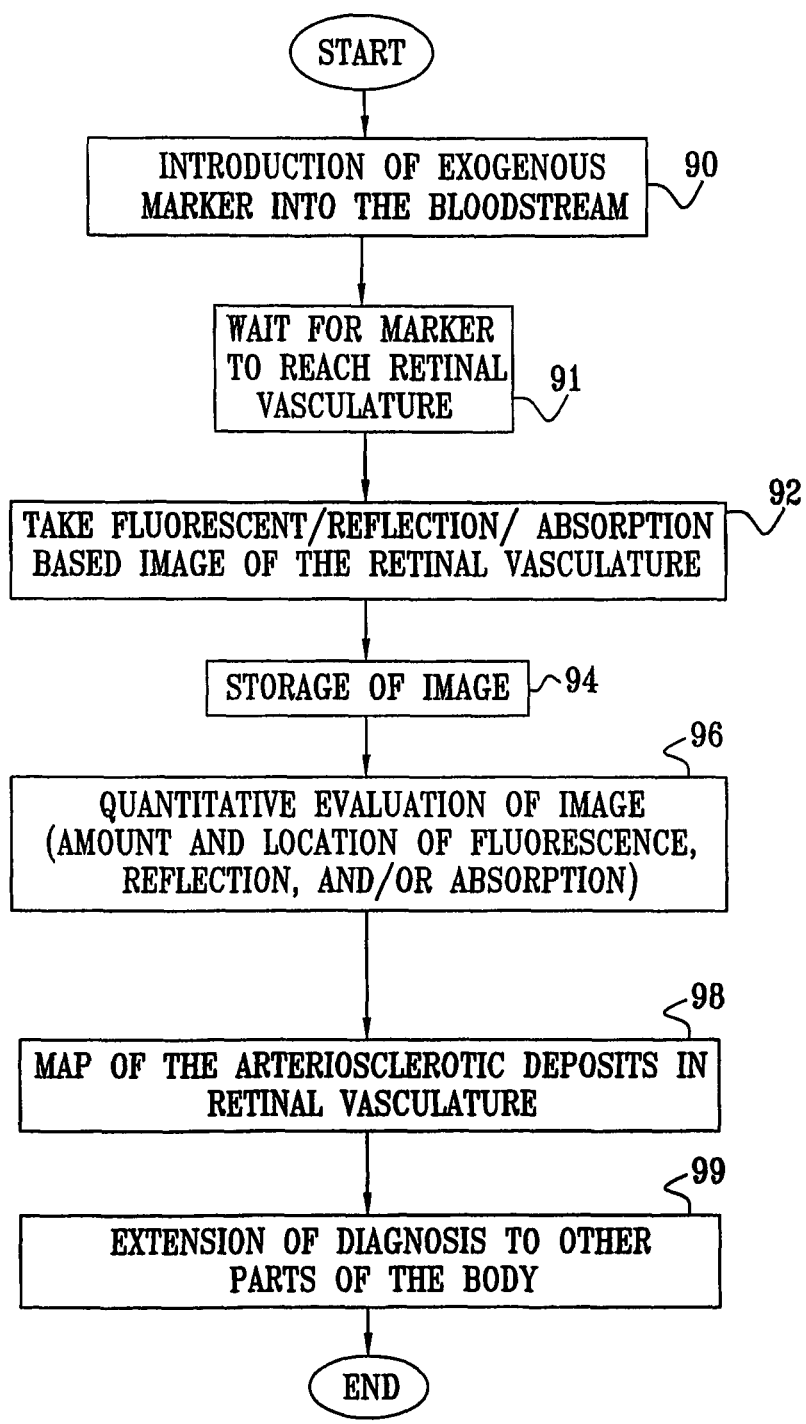
FIG. 6 is a schematic flowchart illustrating the steps taken, in a method according to a further preferred embodiment of the present invention, for the assessment of arteriosclerosis by the imaging of the retinal vasculature after labeling of the arteriosclerotic plaque with an exogenous optically-characterized marker.

Reference is now made to FIG. 6, which is a schematic flowchart illustrating the steps taken, in a method according to a further preferred embodiment of the present invention, for the assessment of arteriosclerosis by the optical imaging preferably of the retinal vasculature after labeling of the arteriosclerotic plaque with an exogenous marker. The main steps are as follows:

Step 90. Introduction of an exogenous marker into the bloodstream, either by oral ingestion and gastro-intestinal absorption, or more preferably, by direct injection.
Step 91. Wait for the marker to reach arteriosclerotic deposits in the retinal vasculature.
Step 92. Take fluorescence/reflection/absorption-based image preferably of the retinal vasculature.
Step 94. Storage of the image.
Step 96. Quantitative evaluation of the image in terms of amount and location of fluorescence, reflection, and/or absorption.
Step 98. Use of quantitative data obtained in step 96 to map arteriosclerotic deposits in the preferably imaged retinal vasculature.
Step 99. Extrapolation of diagnosis made in the preferably imaged retinal vasculature to other parts of the body.

Reference is now made to FIG. 7, which is a schematic drawing of apparatus preferably used for performing the radiation or radio-opacity imaging to reveal the presence of deposits within the vasculature, by means of computerized tomography, even in areas of the body where the vasculature is not directly accessible. This method is enabled because of the high penetration power of radioactivity. The degree of arteriosclerosis can thus be determined directly in many parts of the body. FIG. 7 illustrates a schematic representation of a preferred arrangement of apparatus suitable for performing such measurements, including a CT system with its imaging unit 100 and its associated control equipment 102, and an optional additional computer system 104 for extracting the vascular imaging information from the CT data 105, so that the level of arteriosclerosis can be determined and preferably displayed 106. It is to be understood that the processing and display of the vascular imaging information could equally well be performed within the CT control unit, if adapted thereto.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for vascular analysis of a subject, comprising the steps of:
   predetermining first and second points in a cardiac cycle, said first and second points corresponding to points in time in the cardiac cycle when blood pressure is different;
   optically imaging moving erythrocytes within at least one optically accessible blood vessel of a subject, when the cardiac cycle of the subject is at the first and second points thereof;
   determining from said optical imaging respective flow characteristics of said erythrocytes in said at least one optically accessible blood vessel, at said first and second points in the subject's cardiac cycle;
   identifying roughness on an inner wall of said at least one optically accessible blood vessel, by comparing said flow characteristics to one another; and
   generating an output on an output device, in response to identifying said roughness.

2. A method according to claim 1, wherein said at least one optically accessible blood vessel is a retinal blood vessel of the subject, and wherein optically imaging moving erythrocytes within the blood vessel comprises optically imaging moving erythrocytes within the retinal blood vessel.

3. A method according to claim 1, and wherein said at least one optically accessible blood vessel of the subject is a blood vessel located in tissue of an internal organ of the subject, and wherein optically imaging moving erythrocytes comprises optically imaging moving erythrocytes within the blood vessel located in the tissue.

4. A method according to claim 3, and wherein said tissue is selected from the group consisting of esophageal tissue, gastro-intestinal tissue, brain tissue and tissue of an internal surface of a passageway of the subject, and wherein optically imaging moving erythrocytes comprises optically imaging moving erythrocytes within the blood vessel located in the selected tissue.

5. A method according to claim 1, wherein said identifying comprises identifying the presence of the roughness on the inner wall of the subject's blood vessel non-invasively.

6. A method according to claim 1, wherein said optical imaging comprises acquiring at least two sequential images of erythrocytes in said at least one optically accessible blood vessel.

7. A method according to claim 1, further comprising the step of utilizing said identifying of said roughness on said inner wall of said at least one optically accessible blood vessel in order to determine a condition of another blood vessel of the subject.

8. A method according to claim 1, further comprising the step of utilizing said identifying of said roughness on said inner wall of said at least one optically accessible blood vessel in order to determine a level of arteriosclerosis in the subject.

9. A method according to claim 1, and wherein said flow characteristics of said erythrocytes includes a flow characteristic selected from the group consisting of: mean curvature of motion lines of said erythrocytes, deviation from cylindrical symmetry of the motion lines of said erythrocytes, spatial density of local turbulences in the motion lines of said erythrocytes, and local deviations from the global character of the motion lines of said erythrocytes, and wherein determining the flow characteristics comprises determining the selected flow characteristic.

10. A method for vascular analysis of a subject, comprising the steps of:
   (i) optically imaging moving erythrocytes within at least one optically accessible blood vessel of a subject having a first blood pressure, said first blood pressure being subject to change to a second blood pressure;
   (ii) optically imaging moving erythrocytes within said at least one optically accessible blood vessel again when said first blood pressure of said subject has changed to said second blood pressure;
   (iii) determining from said optical imaging of steps (i) and (ii) at least one erythrocytic flow characteristic in said at least one optically accessible blood vessel, at said first and said second blood pressure;
   (iv) utilizing differences in said at least one flow characteristic at said first and said second blood pressure to determine a roughness index of an inner wall of said at least one optically accessible blood vessel; and
   (v) generating an output on an output device, in response to determining said roughness index.

11. A method according to claim 10, and wherein said change from said first blood pressure to said second blood pressure includes a change caused by a cause selected from the group consisting of exercise performed by the subject, and a drug administered to the subject, and wherein step (ii) is performed when said first blood pressure has changed to said second blood pressure as a result of the selected cause.

12. A method according to claim 10, and wherein said first blood pressure corresponds to a first point in a cardiac cycle of the subject, wherein said second blood pressure corresponds to a second point in the cardiac cycle of the subject, and wherein steps (i) and (ii) comprise optically imaging moving erythrocytes within said at least one optically accessible blood vessel when the subject's cardiac cycle is respectively at said first and second points in the subject's cardiac cycle.

13. A method according to claim 12, wherein steps (i) and (ii) comprise detecting a parameter of the subject selected from the group consisting of the subject's cardiac cycle and blood pressure of the subject, and optically imaging the moving erythrocytes in response to the selected parameter.

14. A system for vascular analysis of a subject, comprising:
   (i) a light source for illuminating at least one optically accessible blood vessel of the subject;
   (ii) an imager for acquiring a plurality of images of moving erythrocytes showing sequential spatial distribution of said moving erythrocytes in said at least one optically accessible blood vessel, the imager synchronized to acquire the plurality of images at predetermined first and second points in the subject's cardiac cycle when blood pressure is different;
   (iii) an image discriminator for determining from said plurality of images showing sequential spatial distribution, flow patterns of erythrocytes along said blood vessel, respectively at the first and second points,
   (iv) a flow analyzer for analyzing said flow patterns to determine respective flow characteristics of erythrocytes along said at least one optically accessible blood vessel of the subject at said first and second points in the subject's cardiac cycle; and
   (v) a wall analyzer for determining at least one property of an inner wall of said blood vessel, by comparing said flow characteristics to one another.

15. A system according to claim 14, and wherein the wall analyzer is configured to determine a roughness of the inner wall of said blood vessel by comparing said flow characteristics to one another.

16. A system according to claim 15, further comprising an arteriosclerotic index determiner for utilizing said roughness to determine a level of arteriosclerosis in said at least one optically accessible blood vessel.

17. A system according to claim 16, and wherein said arteriosclerotic index determiner is configured to utilize said roughness to determine an arteriosclerotic condition of another blood vessel of the subject.

18. A system according to claim 14, and wherein said flow characteristics of said erythrocytes includes a flow characteristic selected from the group consisting of mean curvature of motion lines of said erythrocytes, deviation from cylindrical symmetry of the motion lines of said erythrocytes, spatial density of local turbulences in the motion lines of said erythrocytes, and local deviations from the global character of the motion lines of said erythrocytes, and wherein the image discriminator is configured to determine the selected flow characteristics.

19. A system according to claim 14, further comprising a wavelength selector, configured to configure said imager to acquire said images of said at least one optically accessible blood vessel over a limited wavelength band.

20. A system according to claim 19, wherein said wavelength selector is located in an illuminating pathway between said light source and said at least one optically accessible blood vessel.

21. A system according to claim 19, wherein said wavelength selector is located in an imaging pathway between said at least one optically accessible blood vessel and said imager.

22. A system according to claim 19, and wherein said wavelength selector is configured to configure said imager to acquire said images of said at least one optically accessible blood vessel over a limited wavelength band of between 2 and 30 nanometers.

23. A system according to claim 14, and wherein said light source for illuminating said at least one optically accessible blood vessel of the subject is a pulsed source having a pulse to pulse interval of less than 1 second.

24. A system according to claim 23, and wherein said pulsed source has a pulse to pulse interval that is between 5 and 200 milliseconds.

25. A system according to claim 23, and wherein said pulsed source has a pulse to pulse interval that is between 5 and 40 milliseconds.

26. A system according to claim 14, and wherein said light source for illuminating said at least one optically accessible blood vessel of the subject is a continuous source, and said imager is configured to acquire images at predetermined intervals.

27. A system according to claim 14, and wherein said at least one optically accessible blood vessel of the subject is a retinal blood vessel of the subject, and wherein the light source is configured to illuminate the retinal blood vessel.

28. A system according to claim 14, and wherein said at least one optically accessible blood vessel of the subject is a blood vessel located in tissue of an internal organ of the subject, and wherein the light source is configured to illuminate the blood vessel located in the tissue of the internal organ.

29. A system according to claim 28, wherein said tissue is tissue selected from the group consisting of esophageal tissue, gastrointestinal tissue, brain tissue and tissue of an internal surface of a passageway, and wherein the light source is configured to illuminate the blood vessel located in the selected tissue.

* * * * *